(12) United States Patent
Zhang

(10) Patent No.: US 11,162,962 B2
(45) Date of Patent: Nov. 2, 2021

(54) AUTOMATIC ANALYSIS DEVICE AND SAMPLE ANALYSIS METHOD

(71) Applicant: Shenzhen Increcare Biotech Co., Ltd., Shenzhen (CN)

(72) Inventor: Zhen Zhang, Shenzhen (CN)

(73) Assignee: SHENZHEN INCRECARE BIOTECH CO., LTD, Shenzhen (CN)

( * ) Notice: Subject to any disclaimer, the term of this patent is extended or adjusted under 35 U.S.C. 154(b) by 168 days.

(21) Appl. No.: 16/475,788

(22) PCT Filed: Oct. 30, 2017

(86) PCT No.: PCT/CN2017/108328
§ 371 (c)(1),
(2) Date: Jul. 3, 2019

(87) PCT Pub. No.: WO2018/126774
PCT Pub. Date: Jul. 12, 2018

(65) Prior Publication Data
US 2019/0346469 A1     Nov. 14, 2019

(30) Foreign Application Priority Data
Jan. 6, 2017  (CN) .......................... 201710010294.X

(51) Int. Cl.
*G01N 35/02* (2006.01)
*B01L 3/00* (2006.01)
(Continued)

(52) U.S. Cl.
CPC ............ *G01N 35/025* (2013.01); *B01L 3/508* (2013.01); *B01L 9/06* (2013.01); *G01N 33/5304* (2013.01);
(Continued)

(58) Field of Classification Search
None
See application file for complete search history.

(56) References Cited

FOREIGN PATENT DOCUMENTS

| CN | 102998473 A | 3/2013 |
|----|-------------|--------|
| CN | 103599898 A | 2/2014 |

(Continued)

OTHER PUBLICATIONS

Office Action for Chinese Counterpart Application No. 201710010294.X, dated Apr. 23, 2018, which cites to CN103599898 (7 pages).
(Continued)

*Primary Examiner* — Rebecca M Giere
(74) *Attorney, Agent, or Firm* — Kagan Binder, PLLC

(57) ABSTRACT

An automatic analysis device and a sample analysis method. The automatic analysis device (100) comprises: a loading unit (20) for loading a sample and/or a reagent to a reaction vessel; a reaction unit (10) for incubating, and washing and separating reactants in a reaction vessel; a measurement unit (80) for measuring reaction signals in the reaction vessel; and a transferring unit (50) for transferring the reaction vessel between different locations. The device (100) realizes incubation, washing and separation of the reactants in the reaction vessel by utilizing the reaction unit (10) as a center. The measurement unit (80) independent of the reaction unit (10) measures the signals in the reaction vessel.

16 Claims, 8 Drawing Sheets

(51) Int. Cl.
*B01L 9/06* (2006.01)
*G01N 33/53* (2006.01)
(52) U.S. Cl.
CPC ... *B01L 2200/10* (2013.01); *B01L 2300/0609* (2013.01); *B01L 2300/0636* (2013.01)

(56) References Cited

FOREIGN PATENT DOCUMENTS

| | | | |
|---|---|---|---|
| CN | 104345158 A | * | 2/2015 |
| CN | 104345158 A | | 2/2015 |
| CN | 104714042 A | | 6/2015 |
| CN | 106645765 A | | 5/2017 |
| CN | 106841644 A | | 6/2017 |
| WO | 2005008219 A2 | | 1/2005 |
| WO | 2012130107 A1 | | 10/2012 |
| WO | 2018126772 A1 | | 7/2018 |
| WO | 2018126775 A1 | | 7/2018 |

OTHER PUBLICATIONS

Unpublished U.S. Appl. No. 16/475,802, filed Jul. 3, 2019.
Unpublished U.S. Appl. No. 16/475,810, filed Jul. 3, 2019.
Unpublished U.S. Appl. No. 16/493,351, filed Sep. 12, 2019.
International Search Report, and English Translation thereof, for International Application No. PCT/CN2017/108328, dated Jan. 23, 2018 (4 pages).
Extended European Search Report for European Counterpart Application No. 17889890.4, dated Jul. 22, 2020, (13 pages).

* cited by examiner

AUTOMATIC ANALYSIS DEVICE AND SAMPLE ANALYSIS METHOD

TECHNICAL FIELD

The present disclosure relates to the field of in-vitro diagnostic apparatus, and more particularly to an automatic analyzer and a sample analysis method.

BACKGROUND

In recent years, with the development of the clinical laboratory and the automation technology, not only the automation level of the clinical laboratory is raised and thus the efficiency of the medical test is increased, but the quality and reliability of the test result is also improved. However, with the increasing amount of the samples to be tested, a large scale automatic test system is continuously required in the clinical laboratory to meet the test requirements, resulting in an increasingly crowded clinical laboratory and rising testing costs. Therefore, it is an urgent problem to be solved by the clinical test to increase the efficiency of the test and ensure the quality of the test result by making full use of the existing laboratory resources while cutting the testing cost under the pressure and challenge from the medical insurance fee control.

For convenience of description, the technical solutions and methods of the present disclosure will be described herein by taking a full-automatic immunoassay analyzer, especially a luminescence immunoassay analyzer, used in the In-Vitro Diagnostics (IVD) as an example. It should be understood by those skilled in the art that the technical solution and method of the present disclosure can also be used for other clinical test automatic devices, such as fluorescence immunoassay devices, electrochemical immunoassay devices, and the like. In a full-automatic immunoassay, an antigen or an antibody to be detected in a human sample is analyzed by correlating an analyte concentration with an optical signal or an electrical signal via a series of cascade amplification reactions by using an antigen or an antibody labeled with an enzyme, a lanthanide element, or other chemiluminescent indicators on basis of an immunoassay reaction of an antigen and an antibody. The full-automatic immunoassay is mainly applied in organizations such as the clinical laboratory in the hospital, an independent laboratory, and a blood test center, etc. for quantitative, semi-quantitative, or qualitative detection of various analytes in human body fluids, so as to diagnose infectious diseases, tumors, endocrine functions, cardiovascular diseases, eugenics and best nurture, autoimmune diseases, and the like. The full-automatic immunoassay analyzer generally consists of a sampling unit, a reaction unit, a supply and waste disposal unit, and a system control unit, and the like. The luminescence immunoassay has become a main technology of the automatic immunoassay due to its advantages of quantitative determination, high sensitivity, good specificity, wide linear range, and high level automation. The full-automatic luminescence immunoassay further includes an enzymatic chemiluminescence, a direct chemiluminescence, and an electrochemiluminescence etc., according to a labeling method and a luminescence system.

Referring to FIGS. 1 to 3, the luminescence immunoassay can be generally divided into a one-step method, a delayed one-step method, and a two-step method according to the assay protocols. The luminescence immunoassay generally comprises main test steps of dispensing a sample and a reagent, mixing reactants, incubation, bound-free separation (B/F separation), dispensing a signal reagent, and measurement, etc. It should be noted that in the present disclosure, the reagent is distinguished from the signal reagent and the incubation is distinguished from the signal incubation for the sake of easy illustration. One reagent is for one assay, in other words, reagents used for different assays generally differ in their formulations, volumes, and numbers of components. For a specific assay, it includes a plurality of components, commonly 2 to 5 components, such as a magnetic particle reagent, an enzyme labeling reagent, a diluent, and the like. For different assay protocols, a plurality of reagent components of one assay can be dispensed at one step or in several steps. When dispensed in several steps, the plurality of reagent components can be respectively defined as a first reagent, a second reagent, a third reagent, and so on in light of the dispensing sequence. The signal reagent is used to generate the measurement signal. Generally the signal reagent is one of common reagents, which are used for all the assays. The incubation of the present disclosure refers to a reaction process of an antigen-antibody or a biotin-avidin within the reactants in a reaction vessel under a constant temperature environment before the reactants entering bound-free separation. More specifically, the one-step method performs the incubation for one time, i.e. one incubation before the bound-free separation. The delayed one-step method performs the incubation for two times, including a first incubation before dispensing the second reagent and a second incubation before the bound-free separation. The two-step method performs the incubation for two times, including a first incubation before a first bound-free separation and a second incubation before a second bound-free separation. The signal incubation refers to a signal enhancement process during a period of reaction time under a constant temperature environment once a signal reagent dispensed into the reaction vessel after the bound-free separation. Depending on the reaction system and luminescence principle, not all tests require the signal incubation. The test requiring the signal incubation generally is a chemiluminescence enzyme immunoassay. The test steps of different assay protocols are described in detail as below.

1) One-step method: Referring to FIG. 1, a sample (S) and a reagent (R) are dispensed, mixed uniformly (some test may not require mixing, which is also applied to other tests and will not be repeated again), and incubated (usually for 5 to 60 minutes). After the incubation is finished, a bound-free separation is performed, the signal reagent is dispensed, and the signal incubation is performed (usually for 1 to 6 minutes), and the measurement is finally performed. It should be noted that some luminescence immunoassays do not require the signal incubation because of the difference of formulation of the some signal reagents. In these immunoassays, the measurement may be directly started during or after the dispensing of the signal reagent. One luminescence immunoassay may require one or more signal reagents. Referring to FIG. 2, the signal reagent includes a first signal reagent and a second signal reagent.

2) Delayed One-step Method: The delayed one-step method is distinguished from the one-step method in that the reagent is dispensed in twice. A first incubation is performed after a first reagent is dispensed and mixed uniformly, and a second reagent is dispensed and mixed uniformly after the first incubation. Compared to the one-step method, the delayed one-step method has one more incubation, one more reagent dispensation, and one more uniform mixing action, and the rest of the sequences are the same as that of the one-step method.

3) Two-step Method: The two-step method is distinguished from the delayed one-step method in that the two-step method has one more bound-free separation step. The other steps are the same as those of the two-step method.

To achieve an automatic test by using the above described methods, the existing technical solutions are specifically as below.

In the first existing technical solution, the incubation, the bound-free separation, and the measurement are arranged separately and independently, respective functions are respectively accomplished by three carousels, and reaction vessels are transferred between different units by a mechanical gripping arm. However, in this technical solution, there are a plenty of components and units and the reaction vessels need to be transferred between these units, which brings problems such as large size, high cost, and complicated workflow.

In the second existing technical solution, the incubation and the measurement are arranged together to form an incubation and measurement unit and the bound-free separation is performed by another separate unit. Although one measurement carousel is reduced in this technical solution compared to the first existing technical solution and it is beneficial to control the overall size and cost to a certain extent, this technical solution has the same problems as the first existing technical solution. In this technical solution, in order to obtain a flexible incubation time period, the control of the incubation and measurement unit is complicated and the controls of the incubation and the measurement are restricted by one another. Consequently, both the high speed automatic test and the flexible signal incubation time are unrealizable.

In the third existing technical solution, the incubation, the bound-free separation, and the measurement are accomplished on a single-ring carousel or a manifold rail. In this technical solution, in order to support a longer incubation time period, except for bound-free separation and measurement positions, the carousel needs to be further provided with a plurality of incubation positions, consequently, the size of the carousel or the manifold rail need to be designed very large to realize a high speed test, which causes difficult manufacture and high cost. Besides, in order to realize the delayed one-step method and the two-step method, at least two sample dispensing mechanisms and at least two bound-free separation devices need to be further provided, thereby increasing the cost of materials, manufacture, and increasing the overall size. On the other hand, the incubation time period is limited by this technical solution so as to cause problems such as a fixed incubation time period and a very long time to give result. Furthermore, not only the required darkroom environment for measurement is difficult to be realized and additional shutter mechanism needs to be provided in this technical solution, but a flexible signal incubation time is unrealizable.

SUMMARY

In order to solve the disadvantages and the problems commonly existed in the prior art, the present disclosure provides an automatic analyzer and a sample analysis method thereof with low manufacturing cost, compact structure, and flexible and efficient test flow or method.

According to one aspect of the present disclosure, an automatic analyzer is provided, including a dispensing unit configured to dispense a sample and/or a reagent into a reaction vessel, a reaction unit configured to perform an incubation and a bound-free separation for reactants in the reaction vessel, a measuring unit configured to measure a reaction signal in the reaction vessel, and a transfer unit configured to transfer the reaction vessel between different positions. The reaction unit includes a rotation device provided with a reaction vessel holder for holding the reaction vessel. The measuring unit includes a measurement carousel provided with a reaction vessel holder for holding the reaction vessel. At least one reaction vessel holder of the rotation device and at least one reaction vessel holder of the measurement carousel are within a range of a horizontal movement of the transfer unit.

According to another aspect of the present disclosure, a sample analysis method is provided, including a dispensing step, dispensing a sample and a reagent into a reaction vessel; an incubation step, incubating the reaction vessel in a reaction vessel holder of a reaction unit; a bound-free separation step, performing a bound-free separation in the reaction vessel in the reaction vessel holders of the reaction unit; a measurement step, measuring a reaction signal in the reaction vessel in a reaction vessel holder of a measuring unit; and a transfer step, transferring the reaction vessel between the reaction unit and the measuring unit by a horizontal movement of a transfer unit.

In the present disclosure, the incubation and the bound-free separation of the reactants in the reaction vessel revolves around the reaction unit, the signal in the reaction vessel is measured by the measuring unit independent of the reaction unit, and the transfer of the reaction vessel between the reaction unit and the measuring unit is achieved by the horizontal movement of the transfer unit. In the present disclosure, not only the reliability of the transfer of the reaction vessel is improved, a separate bound-free separation carousel is reduced, and the system structure and control flow are simplified, but also the size of the reaction unit can be significantly reduced and a flexible incubation time can be realized. In addition, a darkroom environment is easier to be obtained by using an independent measuring unit, the performance and the reliability of the analyzer are improved, and a flexible signal incubation time can be achieved. In the present disclosure, the operating efficiency of the analyzer is improved and technical problems of the current automatic instrument such as large volume, low throughput, high cost, and poor performance are well solved, therefore not only the laboratory space is saved and the test efficiency is improved, but also it is favor to decrease expenses and relieve the burden of the patients, finally, a lot of natural resources and social resources are saved.

DETAILED DESCRIPTION OF THE EMBODIMENTS

Figure 1:
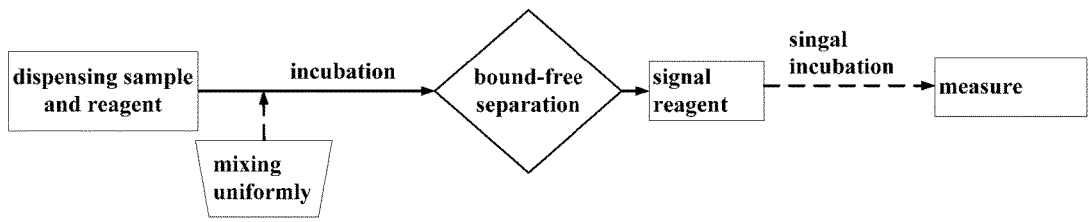
FIG. 1 shows a schematic diagram of a reaction mode of a one-step method.
Figure 2:
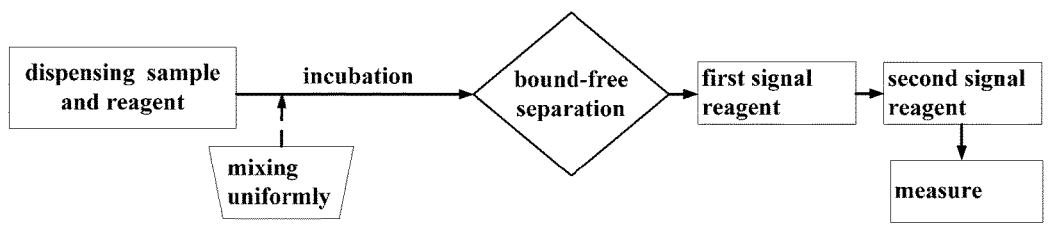
FIG. 2 shows a schematic diagram of a reaction mode of a one-step method (another signal measurement manner)
Figure 3:
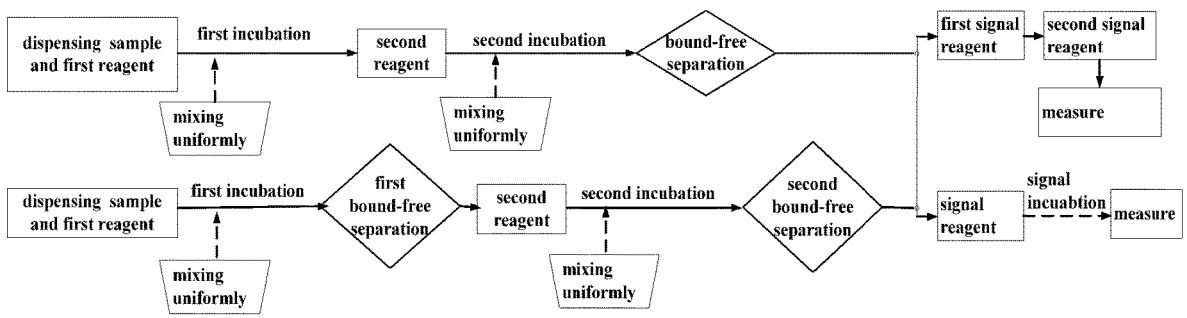
FIG. 3 shows a schematic diagram of reaction modes of a delayed one-step method and a two-step method.

A detailed description with reference to the accompanying drawings is made to further illustrate the present disclosure.

An automatic analyzer according to the present disclosure includes a dispensing unit for dispensing a sample and/or a reagent into a reaction vessel, a reaction unit for performing an incubation and a bound-free separation for reactants in the reaction vessel, a measuring unit for measuring a reaction signal in the reaction vessel, and a transfer unit for transferring the reaction vessel between different positions. The reaction unit includes a rotation device provided with a reaction vessel holder for holding the reaction vessel. The measuring unit includes a measurement carousel provided with a reaction vessel holder for holding the reaction vessel. At least one reaction vessel holder of the rotation device and at least one reaction vessel holder of the measurement carousel are within a horizontal movable area of the transfer unit.

The reaction vessel provides a reaction place for a reaction of the sample and the reagent. The reaction vessel can be a reaction tube, a reaction cup, a reaction strip with a plurality of cavities, a reaction chip, and the like, which can be of various shapes and configurations, and is generally disposable. The reaction vessel is generally made of a plastic such as polystyrene and the like. The reaction vessel may be pre-coated with an antigen or an antibody on an inner wall thereof, or may be not coated. A coated magnetic bead or plastic ball may also be pre-placed in the reaction vessel. The storage and the supply of the reaction vessel are performed by a reaction vessel supply unit. There are mainly two ways for the reaction vessel supply unit to store and supply the reaction vessel. One way is in form of a stock bin, in which reaction vessels in packages can be messily put into the stock bin of the reaction vessel supply unit and then be ranked one by one automatically and supplied to the transfer unit by the reaction vessel supply unit. The other way is in form of pre-arrangement, in which reaction vessels are previously arranged on a reaction vessel tray/box or on a reaction vessel shelf/channel, and a chute tray/box of the reaction vessels or a row/column of the reaction vessels can be transported to the target position.

The transfer of the reaction vessel between different positions in the device of the present disclosure can be performed by the transfer unit. The transfer unit can be any suitable mechanism which enables the reaction vessel to be transferred or moved. In the present disclosure, a preferred transfer unit mainly includes a driving mechanism, a horizontally movable mechanical arm, a grip-release mechanism, and other structures. The grip-release mechanism is generally mechanical fingers capable of gripping and releasing the reaction vessel. The horizontally movable mechanical arm can be driven by the driving mechanism to move the grip-release mechanism along X direction, Y direction, X and Y directions, radial direction, peripheral direction, radial and peripheral directions, and other directions so as to move the reaction vessel gripped by the grip-release mechanism to different positions. Except for the horizontal movement, the transfer unit can also move up and down so as to place the reaction vessel to different positions or take the reaction vessel out from different positions. One or more transfer units can be provided according to a test throughput and an overall layout.

The dispensing of the sample and the reagent is performed by the dispensing unit. The dispensing unit is generally composed of a steel needle or a disposable pipette nozzle (tip), an dispensing action driving mechanism, an injector or liquid injection pump, a valve, a fluid pipeline, a washing cup (when the tip is used, there may be no washing cup), and other components. In order to aspirate and dispense sample and reagent, the dispensing unit can move horizontally and vertically. The horizontal movement generally has several movement forms such as rotation, motion in X direction, motion in Y direction, and combinations thereof. One dispensing unit can be provided to dispense both the sample and the reagent, so that the overall structure is more compact and the cost is lower. In order to increase the test throughput, the dispensing unit can further include one or more sample dispensing units and one or more reagent dispensing units. The sample dispensing unit can be used to dispense only the sample or dispense the sample and a part of the reagent. The reagent dispensing unit is used to dispense the reagent.

A dispensing station can be further provided in the present disclosure to facilitate the dispensing operation of the dispensing unit. The dispensing station is located within the horizontal movable areas of the transfer unit and the dispensing unit, or the dispensing station can be moved horizontally into the horizontal movable areas of the transfer unit and the dispensing unit. The dispensing station receives and holds the reaction vessels transferred by the transfer unit and allows the dispensing unit to dispense the sample and the reagent into the reaction vessels. A reaction vessel holder can be provided on the dispensing station to hold the reaction vessel need to be filled with the sample and the reagent. In order to enable the sample and the reagent to be mixed more uniformly and reacted more fully, while simplify the overall structure and reduce the size, a mixing mechanism can be integrated on the dispensing station, so that the reaction vessel after each dispensing can be subjected to ultrasonic mixing, eccentric rotation, or vibration mixing. Alternatively, the mixing mechanism, such as an ultrasonic generator, can also be integrated on the dispensing unit to perform uniform mixing via ultrasonic wave generated by the dispensing unit at the same time as the sample and the reagent are dispensed or after the dispensation is finished. It should be understood by those skilled in the art that the dispensing station may not be integrated with the mixing mechanism and the mixing can also be accomplished by the aspiration and discharge actions of the dispensing unit or by an impact force of dispensing. In order to make the analyzer more compact, the dispensing station can also be integrally integrated into the reaction unit, so that the dispensing station may not be located under the trajectory of the transfer unit.

The reaction unit is used to perform the incubation and the bound-free separation for the reactants in the reaction vessel. The reaction unit mainly includes a heat preservation device, a rotation device, and a bound-free separation device. A periphery of the heat preservation device is generally provided with a heat insulation material, such as insulation cotton, generally enclosing or surrounding a bottom, a periphery, and a top of the rotation device. An inner side of the bottom or a side of the heat preservation device can be provided with a heater and a sensor, the top of the heat preservation device is generally a structure such as a cover plate, which provides a constant temperature incubation environment for the reaction unit and prevents or reduces the heat loss of the reaction unit. Of course, the heater can also be mounted on the rotation device for higher heat transfer efficiency. In addition to providing the incubation environment, the heat preservation device may also support and fix a magnetic field generator of the bound-free separation device to provide a magnetic field for the bound-free separation. A plurality of chutes, grooves, brackets, bases, or other structures suitable for holding the reaction vessel, which are defined as reaction vessel holders, are provided on the rotation device. There is preferably one rotation device, including a driving mechanism, a transmission mechanism, a related control circuit, and the like, so as to control and drive the rotation device to rotate by a fixed angle at a fixed interval (such as one circle or period), thereby carrying the reaction vessel holder forward by a certain position (such as forward by one reaction vessel holder). At least one reaction vessel holder of the rotation device is located within the horizontal movable area of the transfer unit, so that the reaction vessel can be transferred in and out of the rotation device of the reaction unit by the transfer unit.

The reaction vessel holders of the reaction unit can be classified into two kinds or two types, i.e., a first reaction vessel holder and a second reaction vessel holder, depending on the emphasis and the necessity of main functions achieved. The first reaction vessel holder refers to a reaction vessel holder of the rotation device of the reaction unit capable of carrying the reaction vessel to the bound-free separation device for the bound-free separation. The first reaction vessel holder is mainly used to receive the reaction vessel which is about to subject or is subjecting the bound-free separation. The second reaction vessel holder refers to a reaction vessel holder except for the first reaction vessel holder of the rotation device of the reaction unit. The second reaction vessel holder is the main place for the reaction and incubation of the reaction mixture in the reaction vessel, resulting in the reactions between the analytes in the sample and reagents as well as between the reagents in the reaction vessel. Generally, the more the second reaction vessel holders, the longer the incubation time period can be available, and the higher the test throughput. If the bound-free separation is about to be performed on the reaction vessel after the incubation is finished or performed for a certain time period at the second reaction vessel holder, then the reaction vessel is transferred to the first reaction vessel holder by the transfer unit. It should be noted that although the first reaction vessel holder has the main function to carry the reaction vessel thereon to the bound-free separation device for the bound-free separation via the rotation of the rotation device, the incubation can continue to be performed in the process of the first reaction vessel holder carrying the reaction vessel to the bound-free separation device, and all or part of the signal incubation can be further performed after the first reaction vessel holder carrying the reaction vessel away from the bound-free separation device. Of course, when its number is limited, the first reaction vessel holders may not perform the incubation and signal incubation functions. Regarding the case of all or part of the signal incubation, taken the signal incubation of chemiluminescence enzyme immunoassay as an example, if the signal incubation takes 6 minutes, then the first reaction vessel holder can achieve a full 6 minutes of the signal incubation or only 3 minutes of the signal incubation, and the rest of the signal incubation can be performed at the measuring unit. Of course, the first reaction vessel holder may not perform the signal incubation, and the signal incubation may be completely performed by the measuring unit. In addition, according to the design requirements and the specific layout considerations, when the number of the first reaction vessel holders is large and sufficient, the incubation may also be performed completely by the first reaction vessel holder and no second reaction vessel holder may be provided for the reaction unit.

Except for the functions described above, the bound-free separation device on the reaction unit can further perform the bound-free separation in the reaction vessel in the first reaction vessel holder so as to remove an unbound component from the reactants. The bound-free separation device of the reaction unit of the present disclosure includes a magnetic field generator and a washing mechanism. The magnetic field generator provides a magnetic field for capturing paramagnetic particles in the reaction vessel to the inner side wall of the reaction vessel. The moving of the paramagnetic particles to the inner wall of the reaction vessel takes a certain time period, generally varying from few seconds to tens of seconds, due to factors such as a response time, a moving distance, and a resistance in the magnetic field, so that the reaction vessel needs to pass through the magnetic field for a period of time before each aspiration of waste liquid (including the unbound component). In a preferred embodiment of the present disclosure, the magnetic field generator can be directly mounted or fixed to the heat preservation device of the reaction unit, which not only saves an additional fixing mechanism and reduces the cost, but also brings the magnetic field generator closer to the reaction vessel holder, thereby reducing the collecting time of the paramagnetic particles and improving the efficiency of bound-free separation. The washing mechanism includes a liquid aspiration device and a liquid injection device to aspirate the unbound components in the reaction vessel and inject washing buffer solution into the reaction vessel after the aspiration. The liquid aspiration device includes a liquid aspiration component suitable for aspirating liquid, such as a liquid aspiration needle, tube, nozzle, or the like. The liquid aspiration component is disposed above the reaction unit and can be driven by the driving mechanism to move in and out of the reaction vessel in the reaction vessel holder so as to aspirate the unbound component in the reaction vessel. The liquid injection device includes a liquid injection component suitable for discharging and injecting liquid, such as a liquid injection needle, tube, nozzle, or the like. The liquid injection component is also disposed above the reaction vessel holder of the reaction unit to inject the washing buffer solution into the reaction vessel after the aspiration. Each washing includes one liquid aspiration and one injection of the washing buffer solution. Generally there are three or four washing, i.e. the washing is performed for three or four times. Of course, the number of the washing can be flexibly varied. In order to wash thoroughly with less residuals, a mixer can be further provided at the liquid injection position to mix the reaction vessel uniformly, or an impact force of the liquid injection can be utilized to re-suspend or disperse the paramagnetic particles uniformly in the washing buffer solution when injecting the washing buffer solution or after the injection of the washing buffer solution. When the reaction vessel is carried to the bound-free separation device by the rotation device of the reaction unit, the bound-free separation device begins to perform the bound-free separation in the reaction vessel. Moreover, in order to simplify the mechanism, a signal reagent dispensing mechanism can be further coupled with the bound-free separation device. All or part of the signal reagent, such as all of first and second signal reagents or only the first signal reagent, are dispensed into the reaction vessel once the bound-free separation in the reaction vessel is finished, and the rest of the signal reagent can be dispensed when performing the measurement. In this way, the functions of the bound-free separation device can be fully utilized, thereby reducing the mechanism volume and saving the cost.

It can be seen from the above description that the bound-free separation device is disposed around or above the rotation device of the reaction unit, so that the bound-free separation can be directly performed in the reaction vessel in the rotation device of the reaction unit. In this way, an independent bound-free separation rotation device, such as an independent bound-free separation carousel or rail, is reduced, consequently, not only the assembly and the overall mechanism are simplified, the overall mechanism is more compact, and the cost is lower, but also the transfer of the reaction vessel between the independent bound-free separation device and the reaction unit is avoided and the overall control flow is more simple and effective, thereby improving the operating efficiency and the reliability.

The measuring unit is used to measure a signal in the reaction vessel. The signal is an electrical signal, a fluorescence signal, a weak chemiluminescence signal, or the like generated after the signal reagent is dispensed to the reaction vessel. The measuring unit of the present disclosure is independent of the reaction unit and mainly includes a measurement carousel, an enclosing device, and a measuring device, and the like. The measurement carousel includes at least one ring of reaction vessel holders centered on a rotation center of the measurement carousel for holding the reaction vessels. In order to facilitate the dispensing of the dispensing unit and reduce devices such as the dispensing station as much as possible, the reaction vessel holder of the measurement carousel may be further provided with a sample and/or reagent dispensing position to perform the dispensing of the sample and/or the reagent. For a test requiring the signal incubation, the reaction vessel holder of the measurement carousel can also achieve all or part of the signal incubation function. The reaction vessel in any one of the reaction vessel holders on the measurement carousel can be rotated to the measuring device for measurement by the rotation of the measurement carousel, thereby achieving flexible signal incubation and improving test flexibility and efficiency. Since the signal to be measured is generally a weak optical signal and is easy to be interfered and influenced by ambient light during the test to cause the measurement inaccurate, an enclosed darkroom environment is necessary to be provided for the measuring unit. The periphery of the measurement carousel is generally enclosed or surrounded by the enclosing device of the measuring unit, providing the measuring unit with the enclosed darkroom environment required for the measurement. In addition, in order to realize the signal incubation function for some tests, a heater and a sensor can also be provided at a side or a bottom of the enclosing device to provide a constant temperature incubation environment for the measuring unit and to prevent or reduce the heat loss of the reaction unit. Of course, the heater can also be mounted on the measurement carousel for higher heat transfer efficiency. The measuring device includes a weak optical detector photomultiplier tube (PMT), or other sensitive photoelectric sensing device capable of converting the measured optical signal to an electrical signal for transmission to a control center. Moreover, in order to increase the efficiency of the measurement and ensure the consistency of the measurement, the measuring device can further include an optical device, such as an optical signal collection and calibration device. In a preferred embodiment of the present disclosure, the measuring device can be connected or mounted on the enclosing device in a common manner. For example, the measuring device can be directly fixed on the enclosing device or can be mounted on the enclosing device via an optical fiber connection. In this way, the signal in the reaction vessel in the reaction vessel holder of the measurement carousel can be directly measured, an independent measurement position is avoided to be disposed, and the transfer of the reaction vessel between the measurement carousel and the measurement position is reduced, so that the overall mechanism is more compact, the cost is lower, the control flow is more simple and efficient, and the processing efficiency and reliability are higher. Furthermore, in order to facilitate the dispensing of the signal reagent, the measuring unit of the present disclosure can further include a signal reagent dispensing mechanism to dispense all or part of the signal reagent into the reaction vessel in the reaction vessel holder of the measurement carousel. The measuring unit of the present disclosure is independent of the reaction unit, so that not only the darkroom environment is easier to be obtained, but also the signal incubation is more flexible, therefore the disadvantages of the prior art, such as complicated darkroom structure and fixed signal incubation time period, can be solved.

Furthermore, in order to transport the sample and store the reagent, the automatic analyzer of the present disclosure can further be provided with units such as a sample transport unit, a reagent storage unit, and the like.

The sample transport unit is used to place a sample tube to be detected and transport a target sample tube to a sample aspiration position. The sample transport unit has three main manners, i.e., sample presenting railway, sample presenting carousel, and fixed sample presenting area. The sample tube is generally placed on a sample rack. Each sample rack is generally used to place 5 or 10 sample tubes. The sample rack is placed on a transport railway, a sample carousel, or a fixed area of the analyzer.

The reagent storage unit is used to store the reagent under refrigeration and carry the target reagent to a reagent aspiration position. The reagent storage unit generally adopts two forms, i.e., a reagent carousel and a fixed reagent storage area. In order to ensure the stability of the reagent, the reagent carousel generally has a refrigeration function, for example, 4° C. to 10° C. Generally several reagent pack positions are provided on the reagent carousel to place the reagent pack. Each reagent pack is provided with several independent cavities to store different reagent components, such as a magnetic particle reagent, an enzyme labeled reagent, a diluent, and other reagent components.

Figure 4:
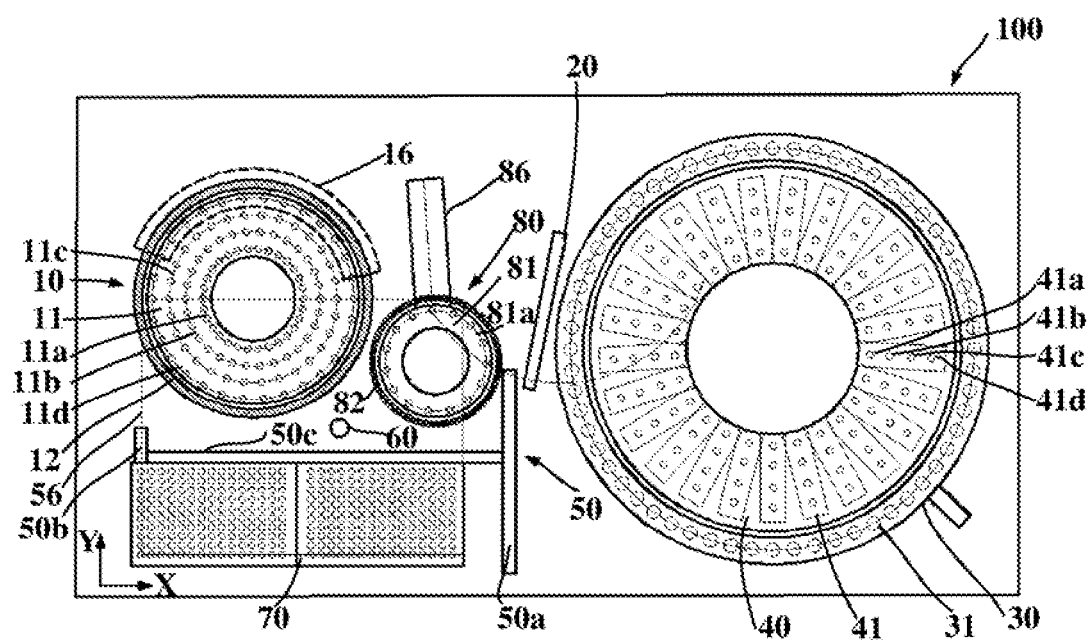
FIG. 4 shows a schematic diagram of an automatic analyzer of a first embodiment of the present disclosure.

Referring to FIG. 4, a first embodiment of the present disclosure provides an automatic analyzer. The automatic analyzer 100 includes a sample transport unit 30, a reagent storage unit 40, a dispensing unit 20, a reaction vessel supply unit 70, a transfer unit 50, a reaction unit 10, a measuring unit 80, and so on. The functions and effects of the units are described as below.

The sample transport device 30 is used to place a sample tube 31 to be tested and transport a target sample tube to a sample aspiration position. In the present embodiment, the sample transport unit 30 is a sample carousel on which an arched sample rack (not shown) is placed, and each arched sample rack has ten sample tubes 31 placed thereon. The sample carousel can be driven by a driving mechanism to carry the target sample to the sample aspiration position under the control of a control center. The sample aspiration position is located at an intersection of a horizontal movement trajectory of the dispensing unit 20 and a center circle of the sample tube.

The reagent storage unit 40 is used to store a reagent pack 41 under refrigeration and carry a target reagent to a reagent aspiration position. In the present embodiment, the reagent storage unit 40 is a reagent carousel provided with 25 positions to receive 25 reagent packs 41 (or reagent boxes, or reagent packs, which will be referred as reagent packs hereafter for easier reference). In the present embodiment, each of the reagent packs 41 is provided with four cavities 41*a*, 41*b*, 41*c*, and 41*d* to store reagent components such as a magnetic particle reagent, an enzyme labeled reagent, and a diluent. The reagent carousel can be driven by the driving mechanism to carry the target reagent pack to the reagent aspiration position under the control of the control center. The reagent aspiration position is located at an intersection of the horizontal movement trajectory of the dispensing unit and a center circle of the sample cavity. In the present embodiment, there are four reagent aspiration positions (not shown) corresponding to the corresponding four reagent components.

The dispensing of the sample and the reagent is performed by the dispensing unit 20. The horizontal movable area of the dispensing unit 20 is intersected with the sample position on the sample carousel 30, the reagent position on the reagent carousel 40, and the reaction vessel holder of the measurement carousel 81 of the measuring unit 80 respectively to form the sample aspiration position, the reagent aspiration position, and an dispensing position at respective intersection. In the present embodiment, the dispensing unit is a single sample dispensing mechanism and can move up and down and be horizontally rotated to dispense both the sample and the reagent, so that the overall structure is more compact and the cost is lower. A mixing mechanism, such as an ultrasonic generator, can also be integrated on the dispensing unit 20 to ultrasonically mix the reaction vessel uniformly after each dispensing. In alternative embodiments, the mixing mechanism can be disposed on the measuring unit 80 to ultrasonically mix or vibrationally mix the reaction vessel uniformly after the dispensing. Of course, a mixing mechanism (not shown) independent of the measuring unit 80 can also be provided, after dispensing is finished at the dispensing position, the reaction vessel is carried to a movable area of the transfer unit 50 by the measuring unit 80 and transferred to the mixing mechanism by the transfer unit 50 to be mixed uniformly. The dispensing position is provided on the measuring unit 80 to take full advantage of the reaction vessel holder of the measuring unit 80 and the rotational positioning function thereof, so that an independent dispensing station can be reduced, some mechanisms are saved, the overall cost is lower, and the structure is more compact.

The reaction vessel supply unit 70 is used to store and supply the reaction vessel. In the present embodiment, in order to make the entire analyzer more compact and the cost lower, a pre-arrangement form is adopted by the reaction vessel supply unit. The reaction vessel supply unit 70 includes two reaction vessel trays on which a plurality of reaction vessel holders are provided to store new reaction vessels. The reaction vessel supply unit 70 is located in the horizontal movable area of the transfer unit 50, so that the transfer unit 50 can cover each new reaction vessel in each reaction vessel holder on the tray to provide the new reaction vessel for a new started test.

The transfer unit 50 can move horizontally to transfer the reaction vessel between different positions of the automatic analyzer 100. In the present embodiment, one transfer unit 50 capable of performing three dimensional movement is provided to make the entire analyzer more compact and cost-saving. The transfer unit 50 includes mechanisms such as an X direction movement mechanical arm 50*b*, a Y direction guide rail 50*a*, a Y direction movement mechanical arm 50*c*, a vertical movement mechanism, and mechanical grippers (not shown). The transfer unit 50 can horizontally move the mechanical grippers simultaneously along the X direction and the Y direction. The horizontal movable area of the transfer unit 50 covers the area in a bounding rectangle 56. The transfer unit 50 can transfer the reaction vessel among the reaction vessel supply unit 70, the first reaction vessel holder of the reaction unit 10, the second reaction vessel holder of the reaction unit 10, the reaction vessel holder of the measuring unit 80, and a reaction vessel disposal chute 60. In addition, because that the movement trajectory of the transfer unit 50 covers at least one first reaction vessel holder of the reaction unit 10, the transfer unit can achieve a flexible incubation time period by placing the reaction vessel into different first reaction vessel holders or transferring the reaction vessel from different first reaction vessel holders.

The reaction unit 10 is used to perform the incubation and bound-free separation for the reactants in the reaction vessel. In present embodiment, the heat preservation device of the reaction unit 10 includes a pot 12 and an upper cover (not shown), the rotation device is a reaction carousel 11, and the bound-free separation device is denoted as 16. An inner side of a bottom and a side of the pot 12 is provided with a heater and a sensor to surround a bottom and a periphery of the reaction carousel 11, so as to provide a constant temperature incubation environment for the reaction unit 10 and prevent or reduce the heat loss of the reaction unit 10. In addition to providing the incubation environment, the pot 12 is further used to support and fix a magnetic field generator of the bound-free separation device 16 to provide a magnetic field environment for the bound-free separation. In the present embodiment, the magnetic field generator of the bound-free separation device 16 is a permanent magnet device, so that a stronger and more stable magnetic field environment can be provided. The washing mechanism of the bound-free separation device 16 includes a liquid aspiration device, a liquid injection device, and a mixing mechanism. A signal reagent dispensing mechanism can be further coupled with the bound-free separation device 16 to dispense all or part of the signal reagent into the reaction vessel after the bound-free separation in the reaction vessel in the reaction vessel holder of the reaction unit 10 is finished. The reaction carousel 11 can be rotated about a center axis. Four rings of reaction vessel holders centered on the rotation center are provided on the reaction carousel 11. Of course, the number of rings can be varied, for example, there can be one, two, three, five, or more rings. The reaction vessel holders on the outermost ring 11*d* are the first reaction vessel holders, and the reaction vessel holders on the inner three rings 11*a*, 11*b*, and 11*c* are the second reaction vessel holders. The first reaction vessel holder is used to carry the reaction vessel to the bound-free separation device 16. When the reaction vessel is passing through the bound-free separation device 16, the bound-free separation is performed on the reaction vessel by the bound-free separation device 16. For a test requiring the signal incubation, the reaction vessel after the bound-free separation can be further carried by the first reaction vessel holder to complete all or part of the signal incubation function.

The measuring unit 80 is independent of the reaction unit and is used to measure the signal in the reaction vessel. In the present embodiment, the measuring unit 80 mainly includes a measurement carousel 81, an enclosing device 82, a measuring device 86, and the like. One ring of reaction vessel holders 81a centered on a rotation center of the measurement carousel is provided on the measurement carousel 81 for holding the reaction vessels. An intersection of the reaction vessel holder 81a and the movement trajectory of the dispensing unit 20 is the dispensing position. A plurality of reaction vessel holders are provided in the present embodiment to perform all or part of the signal incubation. Each time the measurement carousel 81 is rotated, the reaction vessel in any one of the reaction vessel holders can be rotated to the measuring device for measurement, and when the signal incubation is required, the flexible signal incubation time can be realized to improve flexibility and efficiency of the test. The periphery of the measurement carousel is enclosed or surrounded by the enclosing device 82 and a heater and a sensor are disposed at a side or bottom of the enclosing device 82, so as to provide a darkroom environment for the measuring device 86 and to provide a constant temperature incubation environment for the reaction vessel holder 81a of the measurement carousel. The measuring device 86 includes a weak optical detector photomultiplier tube (PMT), which is directly mounted on the enclosing device 82 to measure a weak chemiluminescence signal generated after the dispensing of the signal reagent into the reaction vessel. In addition, in order to facilitate the dispensing of the signal reagent, the measuring unit 80 of the present disclosure can be further provided with a signal reagent dispensing mechanism (not shown) to dispense all or part of the signal reagent into the reaction vessel in the reaction vessel holder of the measurement carousel.

Figure 5:
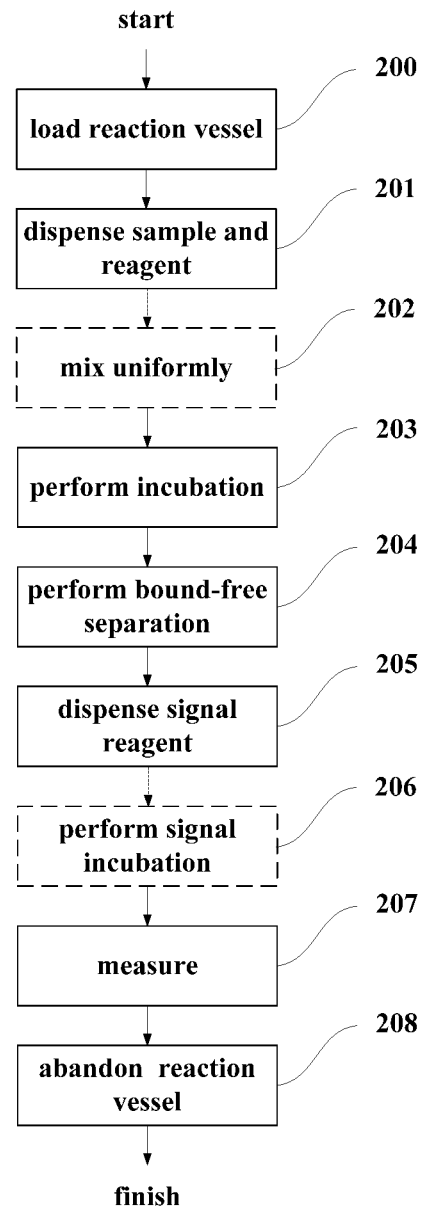
FIG. 5 shows a flow chart of a one-step method.

Take a one-step method as an example, a test flow and steps of the automatic analyzer 100 will now be described with reference to FIGS. 4 and 5. After the test is started:

In step 200 of loading the reaction vessel, one unused reaction vessel is transferred from the reaction vessel supply unit 70 onto the reaction vessel holder of the measuring unit 80 by the transfer unit 50, and the measurement carousel of the measuring unit 80 is rotated to carry the reaction vessel to the dispensing position.

In step 201 of dispensing the sample and the reagent, the sample and the reagent are aspirated from the sample aspiration position and the reagent aspiration position, respectively, and are dispensed into the reaction vessel at the dispensing position of the measuring unit 80 by the dispensing unit 20.

In step 202 of mixing uniformly, if it is required to be mixed uniformly, then the sample and the reagent in the reaction vessel are mixed uniformly by a mixing mechanism integrated on the measuring unit 80, or the reaction vessel filled with the sample and the reagent is transferred out by the transfer unit 50, disposed to a mixing mechanism independent of the measuring unit 80, and mixed uniformly by the mixing mechanism. If it is not required to be mixed uniformly, then this step is omitted.

In step 203 of incubation, the reaction vessel filled with the sample and the reagent is transferred from the reaction vessel holder of the measuring unit 80 or from the mixing mechanism to the second reaction vessel holder of the reaction unit 10 by the transfer unit 50, and the reaction vessel is started to be incubated at the reaction unit. When the reaction vessel is being incubated, the reaction vessel is carried forward by one holder position with the rotation of the reaction carousel 11 at a fixed interval. The incubation time period is varied according to the specific assay and generally is from 5 minutes to 60 minutes.

In step 204 of bound-free separation, when the incubation for the reaction vessel is finished or performed for a period of time, the reaction vessel is transferred from the second reaction vessel holder to the first reaction vessel holder of the reaction unit 10 by the transfer unit 50, the reaction carousel 11 is rotated forward by one holder position at a fixed interval to transfer the reaction vessel in the first reaction vessel holder to the bound-free separation device 2, the reaction vessel is passed through the magnetic field of the bound-free separation device 16, and the liquid aspiration, the injection of the washing buffer solution, the washing, the uniform mixing for the reaction vessel are performed by the washing mechanism and mixing mechanism of the bound-free separation device 16 until the bound-free separation is finished.

In step 205 of dispensing the signal reagent, after the bound-free separation is finished, the reaction vessel in the first reaction vessel holder is transferred away from the magnetic field area by the reaction carousel 11, and all or part of the signal reagent is injected into the reaction vessel by the signal reagent injection mechanism coupled on the bound-free separation device 16, or after being transferred to the measuring unit 80 by the transfer unit 50, all or part of the signal incubation is performed at the reaction vessel holder of the measuring unit 80.

In step 206 of signal incubation, if the signal incubation is required, then all or part of the signal incubation for the reaction vessel is performed at the first reaction vessel holder of the reaction unit 10, or after the reaction vessel is transferred to the measuring unit 80 by the transfer unit 50, all or part of the signal incubation is performed at the reaction vessel holder of the measuring unit 80. If the signal incubation is not required, then this step is omitted.

In step 207 of measurement, after the reaction vessel need to be measured is transferred to the measuring unit 80 by the transfer unit 50, the reaction vessel in the reaction vessel holder is carried to the measuring device 86 by the measurement carousel 81 of the measuring unit 80, the reaction signal in the reaction vessel is measured by the measuring device 86, and the measurement result is processed and then transported to the control center of the automatic analyzer.

In step 208 of abandoning the reaction vessel, the measured reaction vessel is transferred by the transfer unit 50 from the measuring unit 80 to the reaction vessel disposed chute 60 to be abandoned.

Figure 6:
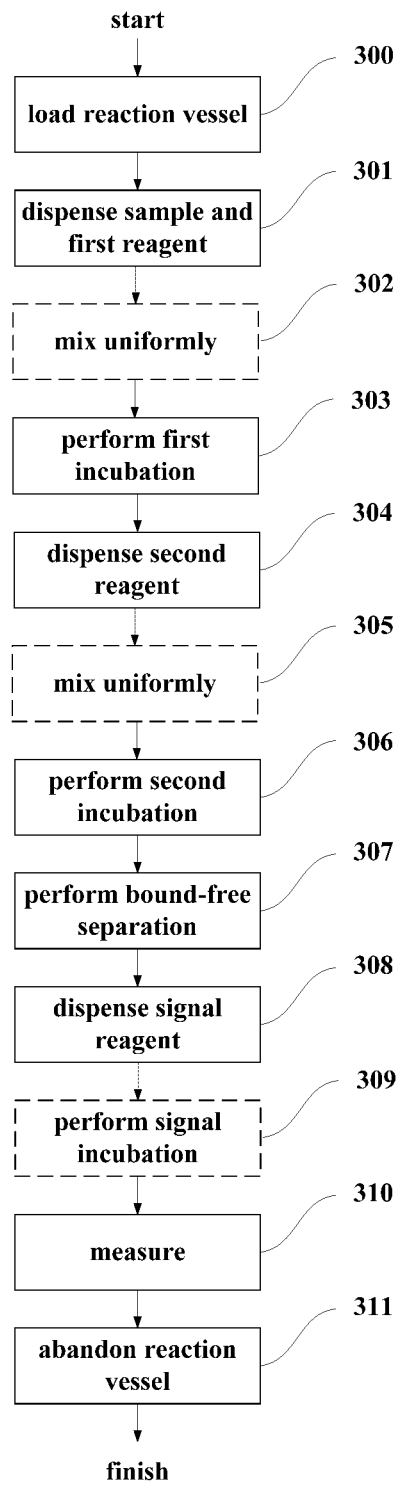
FIG. 6 shows a flow chart of a delayed one-step method.

Referring to FIG. 4 and FIG. 6, the test flow and steps of the delayed one-step method is distinguished from that of the one-step method in that in the steps 301 to 305, the reagent is dispensed in twice and one more incubation is performed. Other steps are the same as that of the one-step method and will not be repeated again.

In step 301 of dispensing the sample and a first reagent, the sample and the first reagent are aspirated respectively from the sample aspiration position and the reagent sample aspiration position and dispensed into the reaction vessel at the dispensing position of the measuring unit 80 by the dispensing unit 20.

In step 302 of mixing uniformly, if it is required to be mixed uniformly, then the sample and the reagent in the reaction vessel are mixed uniformly by a mixing mechanism integrated on the measuring unit 80, or the reaction vessel filled with the sample and the reagent is transferred out by the transfer unit 50, placed to a mixing mechanism independent of the measuring unit 80, and mixed uniformly by the mixing mechanism. If it is not required to be mixed uniformly, then this step is omitted.

In step 303 of incubation, the reaction vessel with the sample and the reagent dispensed is transferred from the reaction vessel holder of the measuring unit 80 or from the mixing mechanism to the second reaction vessel holder of the reaction unit 10 by the transfer unit 50, and the reaction vessel is started to be incubated for the first time at the reaction unit. When the reaction vessel is being incubated for the first time, the reaction vessel is carried forward by one holder position with the rotation of the reaction carousel 11 at a fixed interval. The time period of the first incubation is varied according to the specific test term and generally is from 5 minutes to 60 minutes;

In step 304 of dispensing a second reagent, after the first incubation is finished, the reaction vessel is transferred from the second reaction vessel holder of the reaction unit 10 to the measuring unit 80 by the transfer unit 50 and then carried to the dispensing position by the measurement carousel 81 of the measuring unit 80. The second reagent is aspirated from the reagent aspiration position and injected into the reaction vessel at the dispensing position of the measuring unit 80 by the dispensing unit 20.

In step 305 of mixing uniformly: if it is required to be mixed uniformly, then the reactants in the reaction vessel is mixed uniformly by a mixing mechanism integrated on the measuring unit 80, or the reaction vessel filled with the second reagent is transferred out by the transfer unit 50, placed to a mixing mechanism independent of the measuring unit 80, and mixed uniformly by the mixing mechanism. If it is not required to be mixed uniformly, then this step is omitted.

Figure 7:
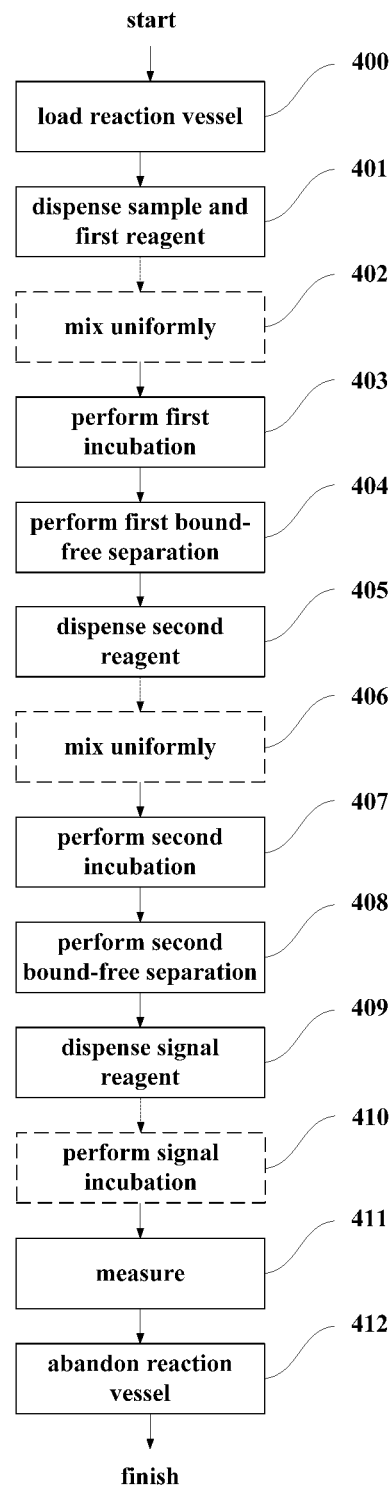
FIG. 7 shows a flow chart of a two-step method.

Referring to FIG. 4 and FIG. 7, a test flow and steps of the two-step method is distinguished from that of the delayed one-step method in that step 404 is added, i.e., one more bound-free separation is added.

In step 404 of bound-free separation, after the first incubation is finished or performed for a period of time, the reaction vessel is transferred from the second reaction vessel holder to the first reaction vessel holder of the reaction unit 10 by the transfer unit 50, the reaction unit 10 is rotated forward by one holder position at a fixed interval to carry the reaction vessel in the first reaction vessel holder to the bound-free separation device 16, the reaction vessel is passed through the magnetic field of the bound-free separation device 16, and the liquid aspiration, the injection of the washing buffer solution, the washing, the uniform mixing for the reaction vessel are successively performed by the washing mechanism and mixing mechanism of the bound-free separation device 16 until the first bound-free separation step is finished. After the first bound-free separation is finished, the reaction vessel is transferred from the first reaction vessel holder of the reaction unit 10 to the reaction vessel holder of the measuring unit 80 by the transfer unit 50 and then carried to the dispensing position by the measurement carousel 81 of the measuring unit 80. The second reagent is aspirated from the reagent aspiration position and dispensed into the reaction vessel at the dispensing position of the measuring unit 80 by the dispensing unit 20.

Other steps of the two-steps method are similar as those of the delay one-step method and will not be repeated again.

As can be seen from the above description, not only a bound-free separation carousel used in the prior art is saved in the automatic analyzer 100, thereby reducing the overall size and decreasing the cost, but also the test step is simplified and the control complexity and control difficulty are decreased, since the transfer of the reaction vessel between a plurality of carousels is avoided. In addition, by providing different reaction vessel holders in the reaction unit, disposing the bound-free separation device on or around the reaction unit, performing the incubation mainly at the second reaction vessel holder, performing the bound-free separation at the first reaction vessel holder, and balancing the number of the first and the second reaction vessel holders, the size of the reaction unit can be further reduced, the overall structure is more compact, the cost is lower, and the test efficiency is higher. By disposing the measuring unit independent of the reaction unit, the darkroom environment can be realized more easily and the overall structure is more simple and compact. Moreover, since the movement trajectory of the transfer unit covers a plurality of second reaction vessel holders of the reaction unit and the measuring unit includes a plurality of reaction vessel holders capable of performing the signal incubation, the flexible incubation and signal incubation time periods can be achieved.

Figure 8:
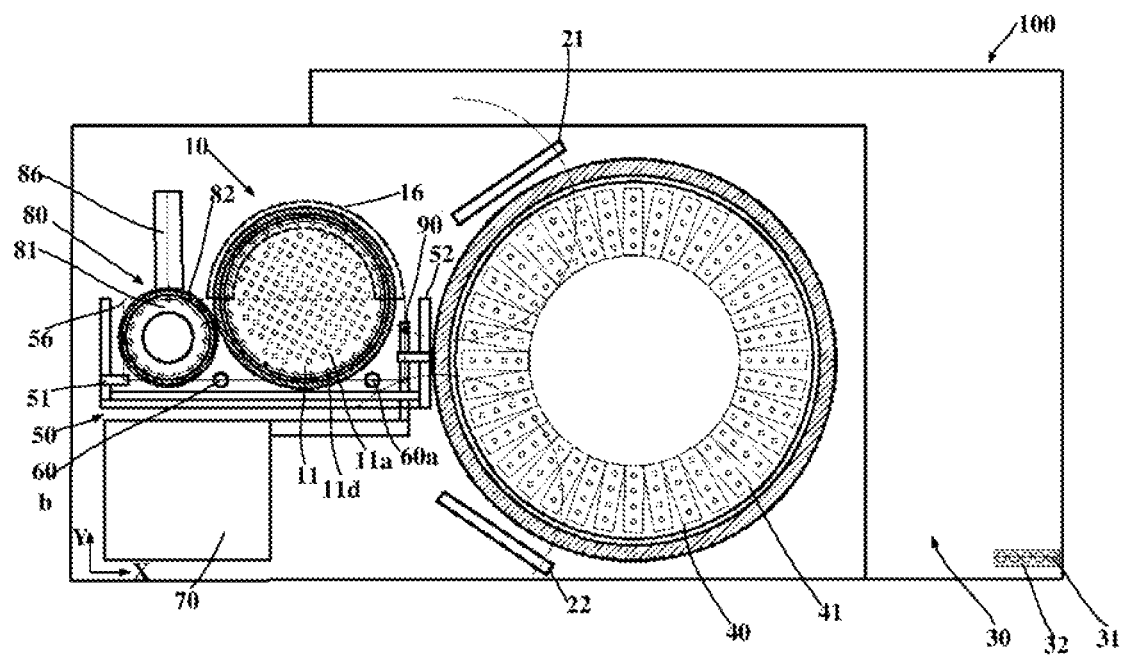
FIG. 8 shows a schematic diagram of an automatic analyzer of a second embodiment of the present disclosure.

Except for the above described unique advantages, the automatic analyzer of the present disclosure can be developed flexibly and reused to a maximum extent to achieve the serialization of products. On the basis of the first embodiment, in order to further enhance the specifications and the test throughput of the analyzer and meet users' requirements for the larger amounts of samples, the number of the transfer units and the dispensing units can be increased, the size and the number of the reaction units can be appropriately increased, or other modification manners can be used. Referring to FIG. 8, FIG. 8 is a schematic diagram of an automatic analyzer of a second embodiment of the present disclosure. The sample transport unit 30 transports the sample by a guide rail and a sample rack so that more samples can be received, the sample can be introduced in real time, and the operation is more convenient. The sample rack 32 and sample tubes 31 on the sample rack 32 can be transported to a movable area of a first dispensing unit 21. The number of the reagent storage positions in the reagent storage unit 40 is increased, so that more reagent packs can be received. The dispensing unit 20 includes the first dispensing unit 21 and a second dispensing unit 22. The first dispensing unit 21 is used to dispense only the sample or to dispense the sample and a part of the reagent. The second dispensing unit 22 is used to dispense the reagent. Of course, more dispensing units can be provided to increase the dispensing speed of the sample and the reagent. The reaction vessel supply unit 70 is in form of the stock bin. The reaction vessels in packages can be messily put into the stock bin of the reaction vessel supply unit 70, in this way, more reaction vessels can be supplied more quickly and more conveniently. The transfer unit 50 includes a first transfer unit 51 and a second transfer unit 52 which can perform three-dimensional movement independently. The first reaction vessel unit 51 mainly transfers the reaction vessel between positions such as the first reaction vessel holder and the second reaction vessel holder of the reaction unit 10 as well as the measuring unit 80 and the reaction vessel dispose chute 60*b*. The second transfer unit 52 mainly transfers the reaction vessel between the reaction vessel supply unit 70, the dispensing station 90, and the reaction unit 10 as well as the reaction vessel dispose chute 60*a*. It should be understood by those skilled in the art that the transfer of the reaction vessel between any two positions can be performed by the first transfer unit or the second transfer unit or both of them via reasonable layout and distribution. Of course, there can be more than two transfer units, and more transfer units can be provided as needed to increase the efficiency and speed of the transfer of the reaction vessel. In order to make the overall layout more compact and increase the test speed, an independent dispensing station 90 is adopted by the present embodiment to dispense the sample and the reagent. The dispensing station 90 can be moved back and forth among the reaction vessel supply unit 70, the first dispensing unit 21, and the second dispensing unit 22 to receive the reaction vessel supplied by the reaction vessel supply unit 70, allow the first dispensing unit 21 to dispense the sample or dispense the sample and a part of the reagent, and allow the second dispensing unit 22 to dispense the reagent. A mixing mechanism can be integrated on the dispensing station 90 or on the dispensing unit 20 to mix the reaction vessel with the sample and the reagent dispensed uniformly. After the uniformly mixing is finished, the reaction vessel on the dispensing station 90 is transferred to the reaction unit 10 by the transfer unit 50. The reaction carousel 11 of the reaction unit 10 includes a first reaction vessel holder area 11$d$ and a second reaction vessel holder area 11$a$. The first reaction vessel holder area 11$d$ is located at an outer edge of the reaction carousel and includes at least one ring of reaction vessel holders centered on the rotation center of the reaction carousel 11. The second reaction vessel holders in the second reaction vessel holder area 11$a$ are distributed on an area on the reaction carousel 11 outside an area where the first reaction vessel holders are located. In the present embodiment, the second reaction vessel holders are located inside of the reaction carousel 11 and distributed in a honeycomb shape, so that space on the reaction unit 10 can be sufficiently utilized to dispose more second reaction vessel holders to receive more reaction vessels, thereby increasing the test flux. The measuring unit 80 is independent of the reaction unit and includes the measurement carousel 81, the enclosing device 82, the measuring device 86, and the like. The measuring unit 80 can be substantially the same as that of the first embodiment except that no dispensing position is provided so as to increase the test efficiency. At least one reaction vessel holder of the reaction carousel 11 and at least one reaction vessel holder of the measurement carousel 81 are within the horizontal movable area of the transfer unit 50 so that the reaction vessel can be transferred between the reaction unit and the measuring unit by the transfer unit 50.

It should be understood by those skilled in the art that the test flow and steps of the present embodiment is distinguished from that of the first embodiment mainly in that the dispensing of the sample and the reagent is performed coordinately by the first and second dispensing units, the transfer of the reaction vessel is performed coordinately by the first and second transfer units, and the dispensing operation of the dispensing unit is performed at the independent dispensing station. Other operations and the rest of the flow are the same or similar as those of the first embodiment, referring to FIG. 5 to FIG. 7, which will not be repeated again. Compared to the prior art, in the present embodiment, additional large size bound-free separation carousel is reduced, the darkroom environment and the flexible measurement can be more easily to be realized by using the independent measuring unit. In addition, the size of the reaction unit itself is also reduced by partitioning or classifying the reaction vessel holders according to different functions, so that the entire analyzer is more compact, the cost is lower, the efficiency is higher, and the reliability is better.

Figure 9:
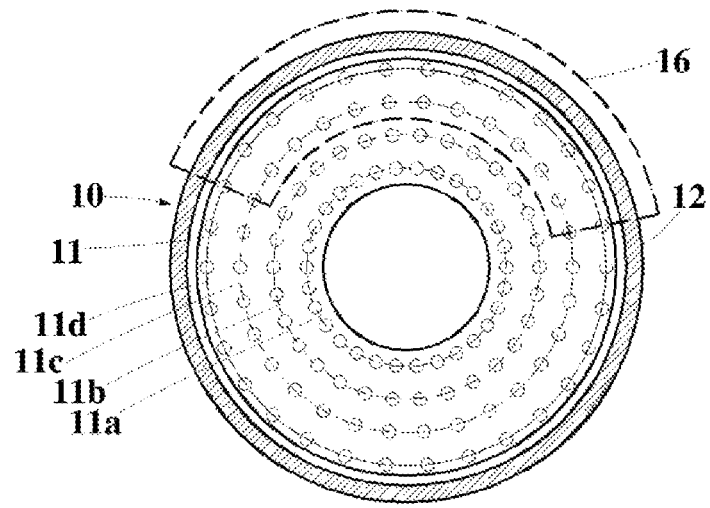
FIG. 9 shows a schematic diagram of a reaction unit of a third embodiment of the present disclosure.
Figure 10:
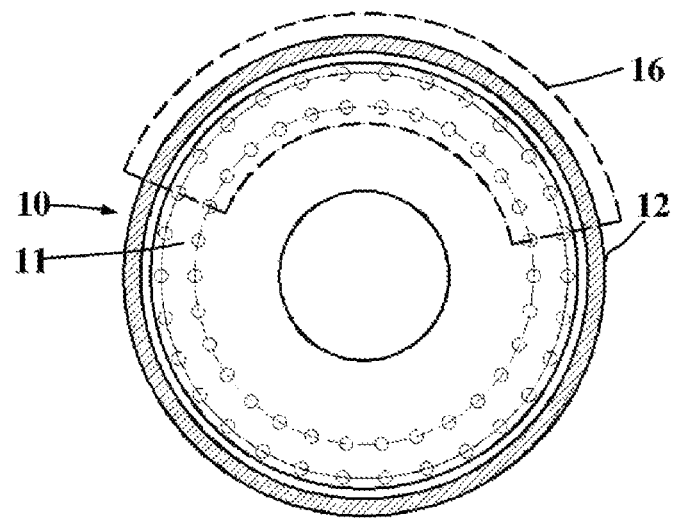
FIG. 10 shows a schematic diagram of a reaction unit of a fourth embodiment of the present disclosure.
Figure 11:
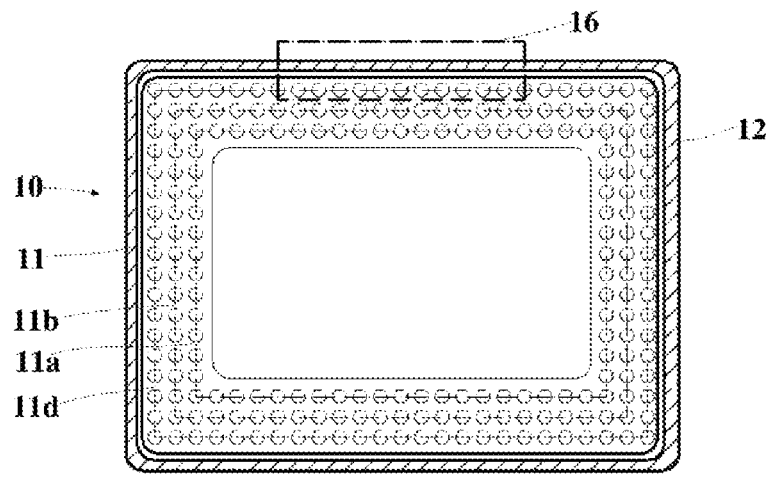
FIG. 11 shows a schematic diagram of a reaction unit of a fifth embodiment of the present disclosure.

Except for the implementation manners described in the first embodiment and the second embodiment of the automatic analyzer of the present disclosure, the reaction unit in the analyzer of the present disclosure can further have various embodiments. Referring to FIG. 9, FIG. 10, and FIG. 11, FIG. 9, FIG. 10, and FIG. 11 are the third, the fourth, and the fifth embodiments of the reaction unit of the analyzer of the present disclosure, respectively. Referring to FIG. 9, in the third embodiment of the reaction unit, the first reaction vessel holders of the reaction unit 10 are located on the outer two rings 11$c$ and 11$d$ centered on the rotation center of the reaction carousel 11 and the second reaction vessel holders of the reaction unit 10 are located on the inner two rings 11$a$ and 11$b$ centered on the rotation center of the reaction carousel 11. The magnetic field generator of the bound-free separation device 16 can be disposed on the pot or other positions between and under the outer two rings 11$c$ and 11$d$. The bound-free separation can be performed simultaneously on the reaction vessels on the outer two rings 11$c$ and 11$d$ by properly dispensing the number of the liquid injection component and the liquid aspiration component of the bound-free separation device 16. In the present embodiment, the bound-free separation can be performed simultaneously on the first reaction vessel holders on the outer two rings 11$c$ and 11$d$ by the bound-free separation device 16, so that the efficiency of the bound-free separation is increased, the problem in the prior art of low efficiency of the bound-free separation or slow test speed of two-step method is solved, and the disadvantages in the prior art such as large volume and high cost due to the requirement for two or more separate bound-free separation devices are avoided. It should be understood by those skilled in the art that the number of the rings of the reaction vessel holders of the reaction unit 10 can be varied, more or less rings of the reaction vessel holders can be disposed, and the number of the rings of the first reaction vessel holders and the second reaction vessel holders can be flexibly and freely combined but not limited to the solution of the present embodiment. Referring to FIG. 10, in the fourth embodiment of the reaction unit, no second reaction vessel holder, but only the first reaction vessel holders are provided. The first reaction vessel holders are located on the inner and outer two rings centered on the rotation center of the reaction carousel 11. The incubation can be performed before the first reaction vessel holder enters into the bound-free separation device 16, the bound-free separation can be performed after the first reaction vessel holder enters into the bound-free separation device 16, and all or part of the signal incubation can be performed after the first reaction vessel holder exits from the bound-free separation device 16. Of course, the reaction unit 10 can be provided with one or more rings of the first reaction vessel holders but no second reaction vessel holder according to the design needs, and this implementation manner is suitable for the test with relative short incubation time period or with low requirement to the test speed. The reaction unit is not limited to be shaped as a carousel, but can be of other shapes or configurations, such as guide rail type or rectangle. Referring to FIG. 11, in the fifth embodiment of the reaction unit, the reaction unit is shaped as a rectangle. Similarly, the reaction unit can include a rotatable device 11 and a heat preservation device 12. The rotation device 11 includes second reaction vessel holder areas 11$a$ and 11$b$ and a first reaction vessel holder area 11$d$. The second reaction vessel holder is mainly used to perform the incubation. The first reaction vessel holder is used to transfer the reaction vessel to the bound-free separation device 16 and the measuring unit 80.

The measuring unit of the present disclosure can also has multiple flexible implementation manners according to differences in factors such as overall structure, layout, and specific component structure as well as factors such as production process and assembly process. Referring to FIG.

Figure 12:
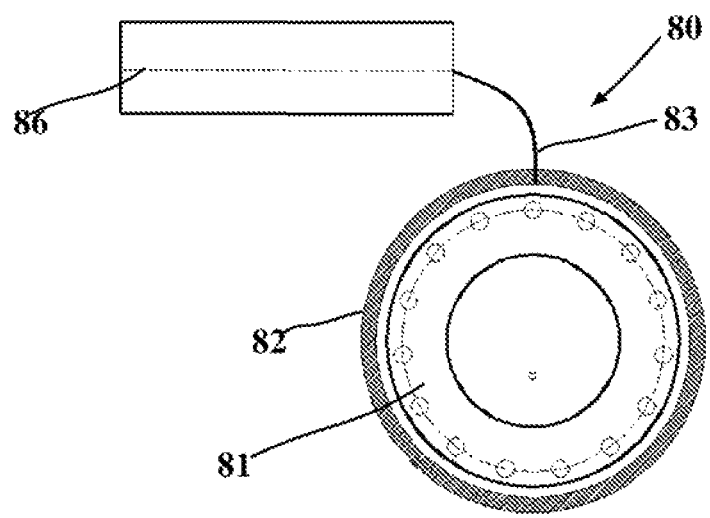
FIG. 12 shows a measuring unit of another embodiment of the present disclosure.
Figure 13:
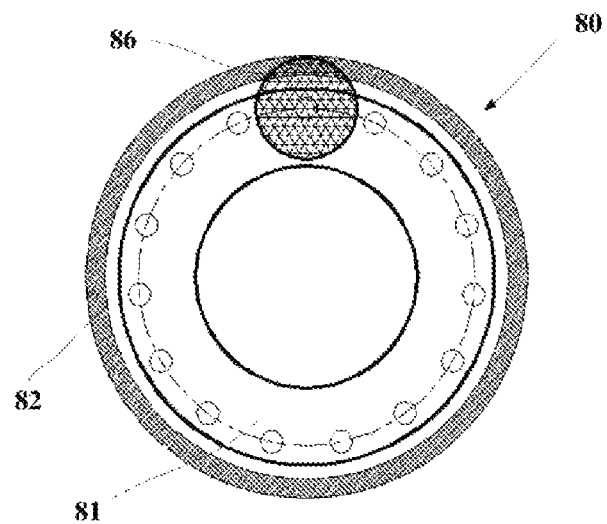
FIG. 13 shows a measuring unit of still another embodiment of the present disclosure.

12 and FIG. 13, FIG. 12 and FIG. 13 are schematic diagrams of another two embodiments of the measuring unit of the present disclosure, respectively. Referring to FIG. 12, in one embodiment, the measuring unit mainly includes a measurement carousel 81, an enclosing device 82, a measuring device 86, and a connection portion 83 between the measuring device 86 and the enclosing device 82. The connection portion 83 can be a signal transmission device such as an optical fiber. One end of the connection portion 83 is connected or mounted onto the enclosing device 82 and the other end thereof is connected or mounted to the measuring device 86. In this way, the position of the measuring device 86 in the automatic analyzer 100 can be flexible adjusted and arranged but not limited to the sizes and arrangement locations of the measurement carousel 81 and the enclosing device 82. Referring to FIG. 13, in another embodiment, the measuring device 86 is vertically connected or mounted above the reaction vessel holder of the measurement carousel 81, so that the overall space can be utilized more fully and the overall size can be reduced.

The embodiments of the present disclosure further provide a sample analysis method, specifically including:
a dispensing step of dispensing a sample and a reagent into a reaction vessel;
an incubation step of incubating the reaction vessel in a reaction vessel holder of a reaction unit;
a bound-free separation step of performing a bound-free separation in the reaction vessel in the reaction vessel holder of the reaction unit;
a measurement step of measuring a reaction signal in the reaction vessel in a reaction vessel holder of a measuring unit; and
a transfer step of transferring the reaction vessel between the reaction unit and the measuring unit by a horizontal movement of a transfer unit.

Furthermore, the incubation step is performed on the first reaction vessel holder and/or the second reaction vessel holder of the reaction unit. The method further includes a transfer step of transferring the reaction vessel between the first reaction vessel holder and the second reaction vessel holder by the transfer unit.

In the present disclosure, the incubation and the bound-free separation of the reactants in the reaction vessel revolves around the reaction unit, the signal in the reaction vessel is measured by the measuring unit independent of the reaction unit, and the transfer of the reaction vessel between the reaction unit and the measuring unit is realized by the horizontal movement of the transfer unit. In the present disclosure, not only the reliability of the transfer of the reaction vessel is improved and a separate bound-free separation carousel is reduced so as to simplify the system structure and control flow, but also the size of the reaction unit can be significantly reduced and a flexible incubation time period is obtained. In addition, a darkroom environment is easier to be obtained by using the independent measuring unit, so that the performance and reliability of the analyzer is improved and a flexible signal incubation time period can be achieved. In the present disclosure, the operating efficiency of the analyzer is improved and technical problems of the existing automatic instrument such as large volume, low throughput, high cost, and poor performance are well solved, therefore not only the laboratory space is saved and the test efficiency is improved, but also it is favor to decrease expenses and relieve the burden of the patients, finally, a lot of natural resources and social resources are saved.

The technical features or operation steps illustrated in the embodiments of the present invention can be combined in any proper way. Those skilled in the art may easily understand that the sequence of steps or actions in the methods illustrated by the embodiments of the present invention can be altered. Therefore, unless a certain sequence is specified otherwise, any sequence in the figures or the detailed description is merely for the purpose of illustration and not an obligatory sequence.

The steps comprised in the embodiments of the present invention can be embodied as executable instructions which can be executed by general or special computer (or other electronic equipments). Optionally, these steps can be executed by a hardware component including a specific logical circuit configured to execute these steps or these steps can be executed by a combination of a hardware, a software, and/or a firmware.

The present invention is illustrated by, but not limited to, the above-described specific embodiments. It should be understood by those skilled in the art that various modifications, equivalents, or variants can also be made without departing from the conception of the present invention, which is within the claimed scope of the present invention. In addition, the phrase of "one embodiment" and "the present embodiment" may represent different embodiments, and all embodiments or a part of them can be combined in one embodiment.

What described above are only several implementations of the present invention, and these embodiments are specific and detailed, but not intended to limit the scope of the present invention. It should be understood by the skilled in the art that various modifications and improvements can be made without departing from the conception of the present invention, and all fall within the protection scope of the present invention. Therefore, the patent protection scope of the present invention is defined by the appended claims.

What is claimed is:

1. An automatic analyzer, comprising:
a dispensing unit configured to dispense a sample and/or a reagent into a reaction vessel;
a reaction unit configured to perform an incubation and a bound-free separation for reactants in the reaction vessel;
a measuring unit configured to measure a reaction signal in the reaction vessel; and
a transfer unit configured to transfer the reaction vessel between different positions;
wherein the reaction unit comprises a rotation device provided with a reaction vessel holder for holding the reaction vessel; the measuring unit comprises a measurement carousel provided with a reaction vessel holder for holding the reaction vessel; at least one reaction vessel holder of the rotation device and at least one reaction vessel holder of the measurement carousel are in a horizontal movable area of the transfer unit;
wherein the reaction vessel holder of the reaction unit comprises a first reaction vessel holder configured to transfer the reaction vessel for a bound-free separation and a second reaction vessel holder configured to perform an incubation for the reactants in the reaction vessel; and
wherein the transfer unit is configured to transfer the reaction vessel among a reaction vessel supply unit, the first reaction vessel holder of the reaction unit, the second reaction vessel holder of the reaction unit, the reaction vessel holder of the measuring unit, and a reaction vessel disposal chute.

2. The automatic analyzer of claim 1, wherein the rotation device is a reaction carousel configured to rotate by a fixed angle at a fixed interval so as to carry the reaction vessel holder of the reaction carousel forward.

3. The automatic analyzer of claim 1, wherein the reaction unit comprises a bound-free separation device configured to perform a bound-free separation for reactants in the reaction vessel in the first reaction vessel holder so as to remove an unbound component in the reactants.

4. The automatic analyzer of claim 2, wherein a plurality of first reaction vessel holders are distributed on at least one ring centered on a rotation center of the reaction carousel, and a plurality of second reaction vessel holders are distributed on at least one another ring centered on the rotation center of the reaction carousel.

5. The automatic analyzer of claim 2, wherein a plurality of first reaction vessel holders are distributed on at least one ring centered on a rotation center of the reaction carousel, and a plurality of second reaction vessel holders are distributed on the area of the reaction carousel outside the area where the plurality of first reaction vessel holders are located.

6. The automatic analyzer of claim 1, wherein the measurement carousel comprises at least one ring of the reaction vessel holders centered on a rotation center of the measurement carousel.

7. The automatic analyzer of claim 6, wherein the reaction vessel holders on the measurement carousel further has a function of signal incubation.

8. A sample analysis method, comprising:
a dispensing step, comprising dispensing a sample and a reagent into a reaction vessel;
an incubation step, comprising incubating reactants in the reaction vessel in a reaction vessel holder of a reaction unit;
a bound-free separation step, comprising performing a bound-free separation in the reaction vessel in the reaction vessel holder of the reaction unit;
a measurement step, comprising measuring a reaction signal in the reaction vessel in a reaction vessel holder of a measuring unit; and
a transfer step, comprising transferring the reaction vessel between the reaction unit and the measuring unit by a horizontal movement of a transfer unit;
wherein in the transfer step, the transfer unit transfers the reaction vessel among a reaction vessel supply unit, the first reaction vessel holder of the reaction unit, the second reaction vessel holder of the reaction unit, the reaction vessel holder of the measuring unit, and a reaction vessel disposal chute.

9. The sample analysis method of claim 8, wherein the bound-free separation step is performed at the first reaction vessel holder of the reaction unit.

10. The sample analysis method of claim 8, wherein the incubation step is performed at the first reaction vessel holder and/or the second reaction vessel holder of the reaction unit.

11. The sample analysis method of claim 10, further comprising a transfer step, for transferring the reaction vessel between the first reaction vessel holder and the second reaction vessel holder by the transfer unit.

12. The automatic analyzer of claim 1, further comprising a dispensing station located within horizontal movable areas of the transfer unit and the dispensing unit, or adapted to be moved horizontally into the horizontal movable areas of the transfer unit and the dispensing unit.

13. The automatic analyzer of claim 12, wherein the dispensing station is provided with a reaction vessel holder for holding the reaction vessel to be filled with the sample and the reagent.

14. The automatic analyzer of claim 1, further comprising a reaction vessel supply unit located in the horizontal movable area of the transfer unit and configured to store and supply the reaction vessel.

15. The automatic analyzer of claim 14, wherein the reaction vessel supply unit comprises a reaction vessel tray provided with a plurality of reaction vessel holders thereon to store reaction vessels.

16. The automatic analyzer of claim 3, wherein the bound-free separation device is disposed around or above the rotation device so as to perform the bound-free separation directly in the reaction vessel in the rotation device.

* * * * *